(12) United States Patent
Dumoulin et al.

(10) Patent No.: US 9,625,545 B2
(45) Date of Patent: Apr. 18, 2017

(54) FARADAY CAGE FOR MR IMAGING WITH ACCESSORY EQUIPMENT

(71) Applicant: Children's Hospital Medical Center, Cincinnati, OH (US)

(72) Inventors: Charles L. Dumoulin, Cincinnati, OH (US); Ronald Pratt, Erlanger, KY (US)

(73) Assignee: Childrens Hospital Medical Center, Cincinnati, OH (US)

( * ) Notice: Subject to any disclaimer, the term of this patent is extended or adjusted under 35 U.S.C. 154(b) by 557 days.

(21) Appl. No.: 14/263,077

(22) Filed: Apr. 28, 2014

(65) Prior Publication Data
US 2014/0354279 A1    Dec. 4, 2014

Related U.S. Application Data

(60) Provisional application No. 61/828,355, filed on May 29, 2013.

(51) Int. Cl.
*G01R 33/422* (2006.01)
*A61B 5/00* (2006.01)
(Continued)

(52) U.S. Cl.
CPC .......... *G01R 33/422* (2013.01); *A61B 5/0046* (2013.01); *A61B 5/055* (2013.01);
(Continued)

(58) Field of Classification Search
CPC ..... G01R 33/422; A61B 5/0046; A61B 5/055; A61B 2562/182; A61M 5/1415; A61M 2209/084
See application file for complete search history.

(56) References Cited

U.S. PATENT DOCUMENTS 4,665,364 A    5/1987 Hanawa
4,727,328 A    2/1988 Carper et al.
(Continued)

FOREIGN PATENT DOCUMENTS

WO    96/29932 A1    10/1996
WO    2013/115846 A1    8/2013
(Continued)

OTHER PUBLICATIONS

Extended European Search report from EP application 12867342.3, Jul. 1, 2015; 7 pages.
(Continued)

*Primary Examiner* — Rodney Bonnette
(74) *Attorney, Agent, or Firm* — Baker & Hostetler LLP (57) ABSTRACT

A Faraday cage assembly for use with a Magnetic Resonance (MR) Imaging scanner is deployed inside the MR scanner room. The Faraday cage assembly is configured to accept accessory medical equipment which is desired to be attached to the patient during scanning. Accessory medical equipment can include patient monitoring systems, injector pumps, and intravenous (IV) poles with infusion pumps. Once the accessory medical equipment is placed inside the Faraday cage, radiofrequency (RF) interference emitted by the accessory medical equipment is contained within the cage and cannot significantly degrade MR image quality. The cage may permit non-MR compatible accessory equipment such as infusion pumps to be used without modification or reconfiguration during MR scanning.

58 Claims, 10 Drawing Sheets

(51) Int. Cl.
*A61B 5/055* (2006.01)
*A61M 5/14* (2006.01)

(52) U.S. Cl.
CPC ...... *A61B 2562/182* (2013.01); *A61M 5/1415* (2013.01); *A61M 2209/084* (2013.01)

(56) References Cited

U.S. PATENT DOCUMENTS

| | | |
|---|---|---|
| 5,178,146 A | 1/1993 | Giese |
| 5,394,873 A * | 3/1995 | Kraemer ............. A61B 5/0555 |
| | | 600/523 |
| 5,515,415 A | 5/1996 | Herrmann et al. |
| 5,619,763 A | 4/1997 | Randolph et al. |
| 5,650,724 A | 7/1997 | Yamagata |
| 5,724,970 A | 3/1998 | Votruba et al. |
| 5,792,041 A | 8/1998 | Kobayashi et al. |
| 5,800,335 A | 9/1998 | Koch et al. |
| 6,101,644 A | 8/2000 | Gagneur |
| 6,377,047 B1 | 4/2002 | Wong |
| 6,611,702 B2 | 8/2003 | Rohling et al. |
| 6,718,571 B2 | 4/2004 | Bartels |
| 6,854,140 B2 | 2/2005 | Bartels et al. |
| 7,093,311 B2 | 8/2006 | Gnoyke |
| 7,131,769 B2 | 11/2006 | Vezina |
| 7,216,383 B2 | 5/2007 | Heinl et al. |
| 7,467,004 B2 | 12/2008 | Calderon et al. |
| 7,599,728 B2 | 10/2009 | Feenan |
| 7,634,827 B2 | 12/2009 | Gagneur et al. |
| 7,827,635 B2 | 11/2010 | Wang et al. |
| 7,850,595 B2 | 12/2010 | White |
| 7,869,858 B2 | 1/2011 | Calderon et al. |
| 7,874,030 B2 | 1/2011 | Cho et al. |
| 7,920,910 B2 | 4/2011 | Calderon et al. |
| 8,147,396 B2 | 4/2012 | Srinivasan |
| 8,276,225 B2 | 10/2012 | Kogan et al. |
| 2001/0052168 A1 | 12/2001 | Haase et al. |
| 2002/0104163 A1 | 8/2002 | Reimann |
| 2002/0158720 A1 | 10/2002 | Weyers et al. |
| 2002/0173717 A1 | 11/2002 | Rohling et al. |
| 2003/0153805 A1 | 8/2003 | Gryn et al. |
| 2005/0034237 A1 | 2/2005 | Lenling et al. |
| 2005/0113668 A1 | 5/2005 | Srinivasan |
| 2006/0074294 A1 * | 4/2006 | Williams, Jr. ....... A61B 5/0046 |
| | | 600/420 |
| 2006/0100500 A1 * | 5/2006 | Williams, Jr. ......... A61B 5/055 |
| | | 600/410 |
| 2006/0293589 A1 | 12/2006 | Calderon et al. |
| 2007/0132581 A1 | 6/2007 | Molyneaux et al. |
| 2007/0232894 A1 | 10/2007 | Feenan |
| 2008/0117044 A1 | 5/2008 | Hibbs |
| 2008/0201849 A1 | 8/2008 | Van Es et al. |
| 2009/0009170 A1 | 1/2009 | Tigwell et al. |
| 2009/0027053 A1 | 1/2009 | Decke et al. |
| 2009/0083907 A1 | 4/2009 | Ahlman |
| 2010/0185045 A1 | 7/2010 | Chinn |
| 2010/0245543 A1 * | 9/2010 | Greer .................. G01R 33/283 |
| | | 348/46 |
| 2011/0113555 A1 | 5/2011 | Smith |
| 2011/0145991 A1 | 6/2011 | Bridge et al. |
| 2012/0071745 A1 | 3/2012 | Rapoport |
| 2013/0025054 A1 | 1/2013 | Graw et al. |
| 2013/0109956 A1 | 5/2013 | Rapoport |
| 2013/0137964 A1 * | 5/2013 | Schellenberg ....... A61B 5/0555 |
| | | 600/411 |
| 2013/0150656 A1 | 6/2013 | Falk et al. |
| 2015/0164331 A1 * | 6/2015 | Burgess ................ A61B 5/015 |
| | | 600/410 |

FOREIGN PATENT DOCUMENTS

| | | |
|---|---|---|
| WO | 2013/115847 A1 | 8/2013 |
| WO | 2013/115848 A1 | 8/2013 |

OTHER PUBLICATIONS

Dumoulin, Charles L., et al., Magnetic Resonance Imaging Compatible Neonate Incubator, Magnetic Resonance Engineering, Jun. 28, 2002, vol. 15 (2), pp. 117-128.
PCT International Search Report/Written Opinion, PCT/US2012/052242, mailed Nov. 2, 2012, 8 pages.
PCT International Search Report/Written Opinion, PCT/US2012/052249, mailed Nov. 2, 2012 10 pages.
PCT International Search Report/Written Opinion, PCT/US2012/052260 mailed Nov. 2, 2012, 13 pages.
European Patent Application No. 12867132.8; Extended Search Report; dated Sep. 16, 2015; 6 pages.
European Patent Application No. 12867263.1; Extended Search Report; dated Sep. 16, 2015; 7 pages.

* cited by examiner

FARADAY CAGE FOR MR IMAGING WITH ACCESSORY EQUIPMENT

CROSS REFERENCE TO RELATED APPLICATIONS

The current application claims the benefit of U.S. Provisional Application Ser. No. 61/828,355, filed on May 29, 2013, the disclosure of which is incorporated herein by reference in its entirety.

FIELD OF THE INVENTION

The present disclosure relates generally to hardware used in Magnetic Resonance (MR) imaging systems, and more particularly, to systems and methods for preventing radiofrequency (RF) interference during MR imaging caused by accessory equipment housed in the MR scanner room during scanning.

BACKGROUND

The following background includes information that may be useful in understanding the present subject matter. It is not an admission that any of the information provided herein is prior art or relevant to the presently claimed subject matter, or that any publication specifically or implicitly referenced is prior art.

Magnetic Resonance Imaging (MRI) employs a strong magnetic field that is used to polarize the spin magnetization in a patient's body. The spin magnetization that is most often used in MRI arises from the nuclei of hydrogen atoms within the body. Although the highest concentration of hydrogen atoms within the body is found in water molecules, other compounds found in the body (e.g. lipids, glucose, etc.) are present in sufficient concentration to provide a detectable MR spin magnetization.

When the hydrogen atoms of a patient's body are introduced into the polarizing magnetic field, the spin magnetization of the hydrogen atom nuclei align in one of two states: with the magnetic field, or against the magnetic field. These two states occupy slightly different energy levels in a quantum mechanical system. By convention, the lowest energy level is called the ground state. It should be noted that the population of nuclear spins in the ground state is slightly higher than that of the higher energy state, resulting in a net magnetization of the macroscopic group of nuclei.

The energy difference between the two energy levels is directly proportional to the strength of the polarizing magnetic field. Thus, as the strength of the magnetic field is increased, the energy difference between the two states increases. The energy differences associated with typical MRI systems correspond to electromagnetic waves in the radiofrequency range. The specific frequency associated with the difference is called the Larmor frequency (typically given in MHz). The constant of proportionality that defines the relationship between the polarizing field (typically given in Tesla) and the Larmor frequency is a natural constant called the gyromagnetic ratio. This constant is unique for each MR active element. For Magnetic Resonance Imaging systems used in medicine, polarizing magnetic field fields are typically between 0.5 and 3.0 Tesla. For hydrogen atoms, these polarizing magnetic field strengths result in Larmor frequencies between 21.3 and 127.8 MHz.

If the nuclear spin system immersed in a polarizing magnetic field is subjected to a rotating magnetic field at the Larmor frequency, the spin system will absorb energy and the distribution of nuclear spins in the two energy states will be disturbed. The duration of the rotating magnetic field used to change the distribution of nuclear spins in the two energy states is typically limited, and applied with a strength sufficient to nutate the net spin magnetization from the longitudinal axis (i.e. parallel with the applied polarizing magnetic field) to the transverse plane (i.e. perpendicular to the applied polarizing field). The term "RF pulse" is conventionally used to describe this process since nutation is accomplished with a rotating magnetic field in the radiofrequency range and having a finite duration.

With time, the energy will be emitted by the spin system in a fashion that can be detected with a sensitive pickup coil. This phenomenon is typically called "resonance". The absorption and re-emission of an RF signal is key to the formation of an MR image.

When an MR signal is created, the frequency of the signal is precisely proportional to the strength of the magnetic field experienced by the nuclear spins. If all of the spins in a patient's body are in an identical magnetic field, then all the spins will resonate with the same frequency. Even though signals come from many different portions of the body, the MR imaging system has no way to distinguish one signal from another.

In order to provide spatial encoding of the MR signals (and hence enable the formation of an image), it is useful to create a transient inhomogeneity in the magnetic field. In typical MRI imaging systems this is accomplished with magnetic field gradient coils. Gradient coils typically are designed to create a magnetic field whose strength varies in a linear fashion over a selected volume within the magnet. Gradient coil sets are typically constructed to permit gradient fields to be created in three orthogonal directions within the bore of the magnet. Typical gradient coils driven by typical gradient amplifiers can generate a magnetic field gradient of 20 mT/m in less than 1 ms, and maintain that gradient with high fidelity for an extended period limited only by the heat dissipation of the gradient coils and amplifier.

A typical imaging system creates an image by employing a sequence of RF and magnetic field gradient pulses to establish a detectable MR signal in a selected plane. This signal is then spatially encoded using magnetic field gradient pulses to impart phase and frequency shifts to the MR signal which reveal the location of the signal source within the bore of the magnet. By selecting pulse sequence repetition times (TR), echo times (TE) and other pulse sequence parameters, the operator can tune the pulse sequence to be sensitive to a variety of intrinsic MR parameters found in the tissue of the patient (e.g. longitudinal relaxation time, T1, Transverse relaxation time, T2, and the like). Many pulse sequences are known to those skilled in the state of the art. These pulse sequences can collect data in two or three dimensions. They can also collect data in Cartesian, radial or spiral frameworks.

One aspect common to all MR imaging pulse sequences is that they employ transient magnetic field gradients. These transient gradient pulses are created by running electrical current through the gradient coils that are located within the bore of the magnet. Current running through these coils creates a mechanical force that results in a small physical displacement of the coil and its structure. Because of the temporal duration of these gradient pulses, acoustic noise is created. Despite aggressive engineering measures to minimize the amplitude of these physical displacements, MR imaging systems can be loud and hearing protection for the patient is required.

Because the amplitude of the MR signal detected by the MR scanner receiver system is weak, MR magnets are typically placed inside a screen room which acts as a Faraday cage. All electrical signals into and out of the screen room go through filters located in a penetration panel to prevent stray RF signals entering into the screen room from the outside. In the absence of a Faraday cage, RF interference manifests itself in an MR image as an elevated noise floor and/or "zipper" artifacts. In extreme cases, RF interference can saturate the preamplifiers of the MR imaging system and prevent the acquisition of MR signals. When the door to the screen room is closed, the magnet is surrounded by the conducting surfaces of a Faraday cage and external radiofrequency sources such as two-way radios, computers, infusion pumps and the like cannot interfere with MR image acquisition.

It is often desirable to perform MR imaging in patients who are attached to accessory equipment such as infusion pumps, respirators, and/or anesthesia equipment. In these circumstances it is often not practical to place these pieces of equipment outside the screen room since direct attachment to the patient is necessary. Unfortunately, these types of accessory equipment often create RF noise which can degrade the MR images acquired from the patient.

In view of the foregoing, it may be understood that the reduction of radiofrequency interference during MR scanning is desirable, and may serve to increase the quality of images obtained with Magnetic Resonance. Furthermore, it is desirable to reduce RF interference without modification of the equipment that creates the RF noise.

SUMMARY

Embodiments of the present disclosure provide a portable Faraday cage whose construction serves to attenuate RF noise created by accessory equipment in the MR magnet room. In an exemplary embodiment, the portable Faraday cage has its own penetration panel that provides filtered electrical connections for power and communications into and out of the cage. In an alternate embodiment, the portable Faraday cage is configured to accommodate an Intravenous (IV) pole supporting one or more infusion pumps, a respirator or similar accessory equipment needed for patient life support.

In an exemplary embodiment, one or more waveguides are provided to permit hoses and tubes to be connected to accessory equipment inside the portable Faraday shield while remaining connected to the patient. Waveguides are openings in the Faraday cage that are configured to block RF signals below a selected frequency. A waveguide's length and diameter are design parameters that are chosen to exploit the fact that an electromagnetic field attenuates rapidly down a small diameter hole of sufficient depth. The degree of attenuation depends on frequency, and the lowest frequency that will pass through the waveguide is commonly called the cut-off frequency. With the current embodiment, a general rule of thumb is that cut-off frequency should be chosen to be higher than the Larmor frequency of the MR scanner. In the exemplary embodiment, waveguides may have a split construction that permits the hoses and tubes to be installed in the waveguide without disconnecting the hose or tube from the accessory equipment and patient.

In another exemplary embodiment, the portable Faraday cage has a RF-tight window that permits an operator to see inside the cage to monitor the accessory equipment contained therein.

In an embodiment, an assembly for housing a patient's treatment or monitoring equipment during a patient's Magnetic Resonance (MR) exam, includes: a Faraday cage having an interior sized for receiving a patient's treatment or monitoring equipment, the Faraday cage having a door-opening into the interior and a door adapted to cover the door-opening (the door may be mounted to the door opening by hinges or may be a sliding door or a completely removable door, for example). In a more specific embodiment, the assembly may further include a slot opening and extending into (a) an outer side edge of the door and/or (b) an inner side edge of the door-opening, where the slot provides an opening into the Faraday cage interior when the door is closed that is sized to receive lines (e.g., IV tubes, wires, etc.) extending between the patient and patient's treatment or monitoring equipment. In a further detailed embodiment, the slot may be dimensioned to block RF signals at and below a predetermined frequency. In a further detailed embodiment, the predetermined frequency may be the Larmor frequency of an MR scanner used for the patient's MR exam. Alternatively or in addition, the opening provided by the slot may have a maximum opening width dimension of less than $\frac{1}{4}^{th}$ the wavelength of radio frequency waves at the Larmor frequency of an MR scanner used for the patient's MR exam.

In a further detailed embodiment, the assembly further may include a waveguide assembly mounted thereto and having a waveguide channel extending therethrough and sized to receive lines extending between the patient and patient's treatment or monitoring equipment, where the waveguide channel communicates with the slot opening into the Faraday cage. In a more detailed embodiment, the waveguide assembly may include: an elongated waveguide body having a longitudinal side opening into the waveguide channel for receiving the lines extending between the patient and patient's treatment or monitoring equipment therein; and an elongated cap adapted to mount over the longitudinal side opening of the waveguide body. Alternatively, or in addition, the waveguide assembly may be mounted within the Faraday cage. Alternatively, or in addition, the waveguide assembly may be mounted to one of an inner surface and outer surface of the door. Alternatively, or in addition, the length of the waveguide body may be longer than approximately $\frac{1}{4}^{th}$ the wavelength of radio frequency waves at the Larmor frequency of an MR scanner used for the patient's MR exam. Alternatively, or in addition, the waveguide channel may have a maximum cross-sectional width dimension of less than $\frac{1}{4}^{th}$ the wavelength of radio frequency waves at the Larmor frequency of an MR scanner used for the patient's MR exam.

In a further detailed embodiment, the Faraday cage interior may be sized to receive an accessory equipment assembly including an IV pole, an IV bag holder, an IV bag, and an infusion pump. In a more detailed embodiment, the assembly may further include a ramp providing a slanted surface from a floor surface on which the assembly is situated to a bottom surface of the Faraday cage interior. Alternatively, or in addition, the assembly may further include rollers mounted on an underside surface of the Faraday cage.

In a further detailed embodiment, the Faraday cage may be adapted to be mounted to or hung from an IV pole. In such an embodiment, the Faraday cage may be sized to house an infusion pump.

In a further detailed embodiment, the assembly further may include a power supply, the power supply providing electrical outlets to the Faraday cage interior. In a further detailed embodiment, the power supply may be contained within the Faraday cage interior. Alternatively, or in addition, the power supply may include an external power supply cord and RF filters that substantially limit RF interference from exiting the Faraday cage via the external power supply cord. Alternatively, or in addition, the power supply may include an internal battery providing power to the electrical outlets.

In a further detailed embodiment, the assembly may further include a conductor mounted to the door and/or to the door frame, providing electrical contact between the door and the door frame when the door is closed onto the door frame. In a further detailed embodiment, the conductor may include a plurality of conducting fingers affixed the inside surface of the door and/or the outer surface of the door frame. Alternatively, or in addition, the conductor may include a conductive gasket affixed to the inside surface of the door and/or the outer surface of the door frame.

In a further detailed embodiment, the assembly may further include a window providing visual access to the Faraday cage interior, where the window is formed from a conductive material. In a further detailed embodiment, the window may be provided on the door. In an alternative detailed embodiment, the assembly may further include a window that may be covered by a conductive mesh screen that allows sounds (emitted by the monitoring equipment contained in the Faraday cage, for example) to be heard outside of the cage.

In a further detailed embodiment, the assembly may further include an audio transmission system for transmitting audio sounds emanating from the Faraday cage interior to a point outside of the Faraday cage. In a further detailed embodiment, the audio transmission system may include a microphone positioned within the Faraday cage interior. Alternatively, or in addition, the audio transmission system may include a Bluetooth repeater in electrical communication with the microphone.

In a further detailed embodiment, the Faraday cage may be constructed primarily from non-ferromagnetic materials. In a further detailed embodiment, the non-ferromagnetic materials may include copper, aluminum and/or brass.

In another exemplary embodiment, a method for performing a Magnetic Resonance exam on a patient connected by a line to a piece of medical equipment may include the steps of: (1) providing a Faraday cage assembly including: (a) a Faraday cage having an interior sized for receiving the piece of medical equipment, where the Faraday cage has a door-opening into the interior and a door adapted to cover the door-opening; and (b) a slot opening and extending into (i) an outer side edge of the door and/or (ii) an inner side edge of the door-opening, where the slot provides an opening into the Faraday cage interior when the door is closed that is sized to receive the lines extending between the patient and patient's piece of medical equipment; (2) placing the piece of medical equipment into the Faraday cage interior, (3) inserting the lines extending between the patient and the piece of medical equipment into the slot; (4) closing the door; and (5) performing the MR exam on the patient while the piece of medical equipment is in the Faraday cage interior with the door closed; where the above steps may occur without disconnecting the lines from the piece of medical equipment or from the patient.

Support for invention(s) will now be described in more detail with reference to exemplary embodiments thereof as shown in the accompanying drawings. While support for the invention(s) is provided below with reference to exemplary embodiments, it should be understood that the scope of the invention is not limited thereto. Those of ordinary skill in the art having access to the teachings herein will recognize additional implementations, modifications, and embodiments, as well as other fields of use, which are within the scope of the invention(s) as described herein, and with respect to which the invention(s) may be of significant utility.

BRIEF DESCRIPTION OF THE DRAWINGS

In order to facilitate a fuller understanding of the present invention, reference is now made to the accompanying drawings, in which like elements are referenced with like numerals. These drawings should not be construed as limiting the present invention, but are intended to be exemplary only.

In the drawings.

DETAILED DESCRIPTION

Embodiments of the present disclosure provide a Faraday cage for minimizing radiofrequency (RF) interference from accessory equipment during MR scanning. This Faraday cage is placed inside the MR scanner's screen room and permits the use of RF noise-generating equipment inside the screen room during MR scanning.

MR imaging of internal body tissues may be used for numerous medical procedures, including diagnosis and surgery. In general terms, MR imaging starts by placing a subject in a relatively uniform, static magnetic field. The static magnetic field causes hydrogen nuclei spins to align and precess about the general direction of the magnetic field. Radio frequency (RF) magnetic field pulses are then superimposed on the static magnetic field to cause some of the aligned spins to alternate between a temporary high-energy nonaligned state and the aligned state, thereby inducing an RF response signal, called the MR echo or MR response signal. It is known that different tissues in the subject produce different MR response signals, and this property can be used to create contrast in an MR image. An RF receiver detects the duration, strength, and source location of the MR response signals, and such data are then processed to generate tomographic or three-dimensional images.

Figure 1:
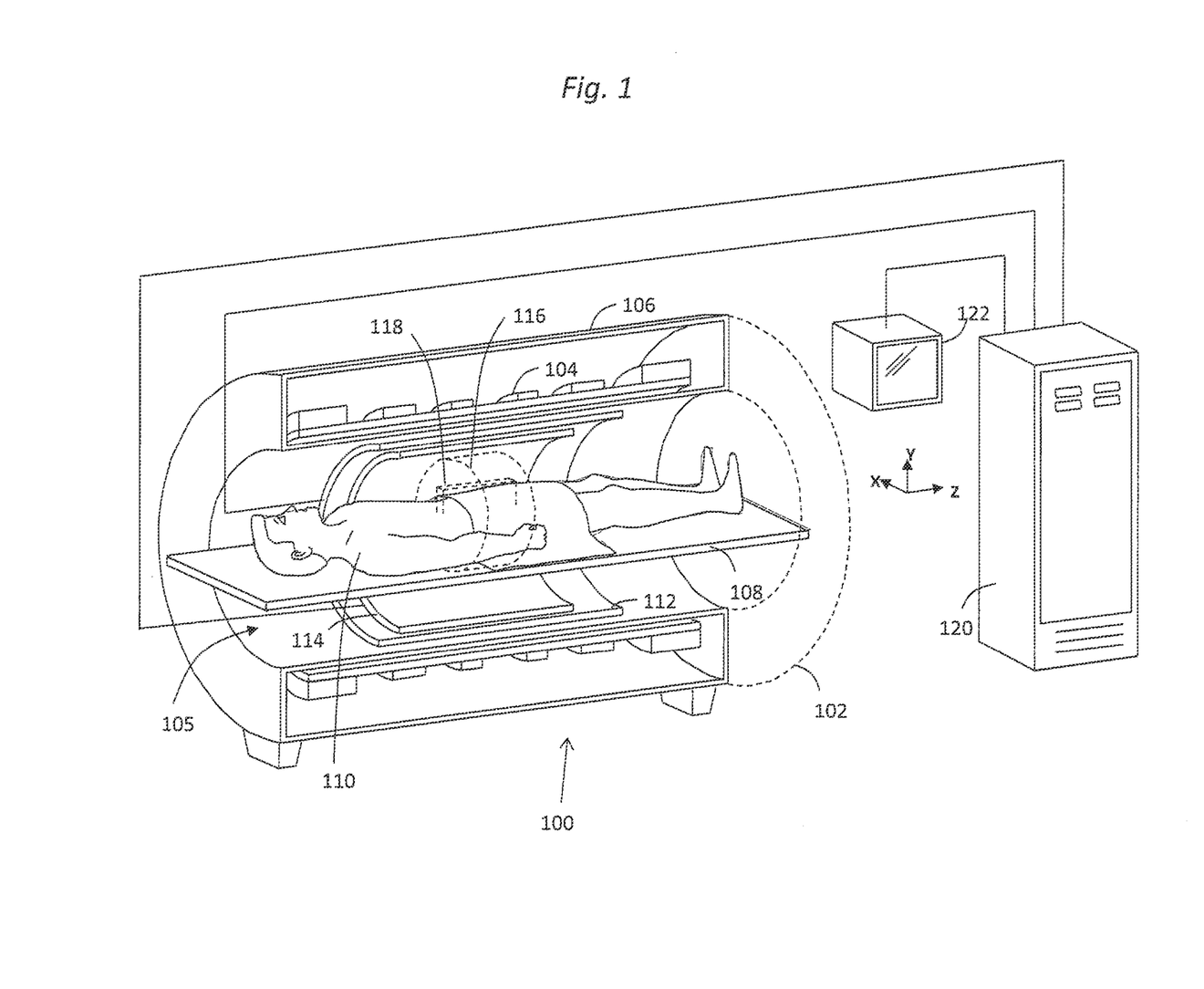
FIG. 1 shows an exemplary MRI system for which the present disclosure may be implemented.

FIG. 1 shows an exemplary MRI system 100 in or for which MR imaging in accordance with the present disclosure may be implemented. The illustrated MRI system 100 comprises an MRI magnet assembly 102. Since the components and operation of the MRI scanner are well-known in the art, only some basic components helpful in the understanding of the system 100 and its operation will be described herein.

The MRI magnet assembly 102 typically comprises a cylindrical superconducting magnet 104, which generates a static magnetic field within a bore 105 of the superconducting magnet 104. The superconducting magnet 104 generates a substantially homogeneous magnetic field within an imaging region 116 inside the magnet bore 105. The superconducting magnet 104 may be enclosed in a magnet housing 106. A support table 108, upon which a patient 110 lies, is disposed within the magnet bore 105. A region of interest 118 within the patient 110 may be identified and positioned within the imaging region 116 of the MRI magnet assembly 102.

A set of cylindrical magnetic field gradient coils 112 may also be provided within the magnet bore 105. The gradient coils 112 also surround the patient 110. The gradient coils 112 can generate magnetic field gradients of predetermined magnitudes, at predetermined times, and in three mutually orthogonal directions within the magnet bore 105. With the field gradients, different spatial locations can be associated with different precession frequencies, thereby giving an MR image its spatial resolution. An RF transmitter coil 114 surrounds the imaging region 116 and the region of interest 118. The RF transmitter coil 114 emits RF energy in the form of a rotating magnetic field into the imaging region 116, including into the region of interest 118.

The RF transmitter coil 114 can also receive MR response signals emitted from the region of interest 118. The MR response signals are amplified, conditioned and digitized into raw data using an image processing system 120, as is known by those of ordinary skill in the art. The image processing system 120 further processes the raw data using known computational methods, including fast Fourier transform (FFT), into an array of image data. The image data may then be displayed on a monitor 122, such as a computer CRT. LCD display or other suitable display.

Figure 2:
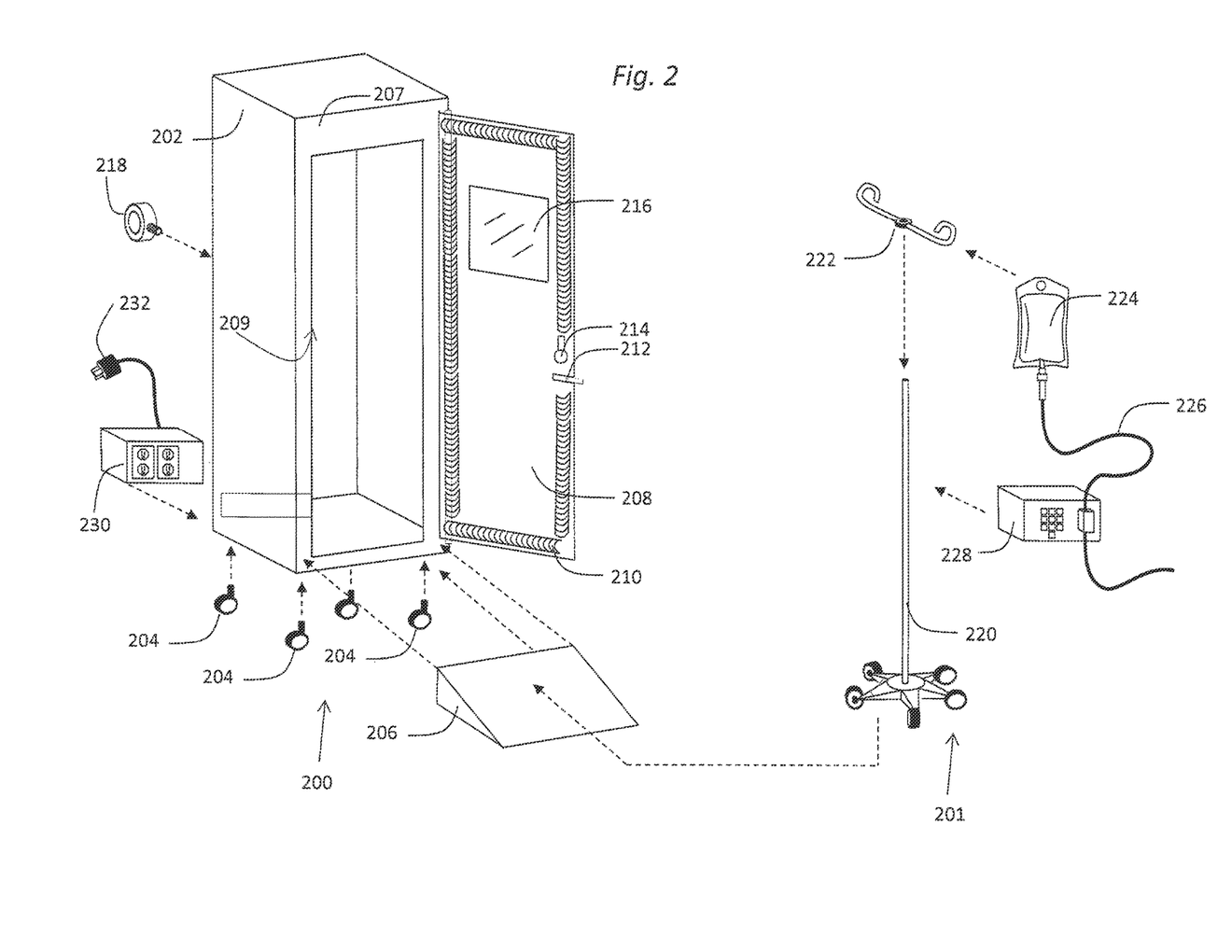
FIG. 2 shows an exemplary portable Faraday cage system suitable for incorporation with an embodiment of the present disclosure.

FIG. 2 illustrates an embodiment of a Faraday cage assembly 200 for containing, for example, an accessory equipment assembly 201 within an MR scanning area. In this illustration, accessory equipment assembly 201 is comprised of an IV pole 220, an IV bag holder 222, an IV bag 224, IV hose 226 and an infusion pump 228. Although shown here as a fluid support station for patient 110, accessory equipment assembly 201 may be comprised of one or more alternate elements such as monitors, injection pumps, respirators, anesthesia equipment and other equipment which are desired to be attached to patient 110 during MR scanning. At least one element of accessory equipment assembly 201 may be assumed to have the potential to emit RF interference that could degrade the quality of the MR images acquired from patient 110. Accessory equipment assembly 201 may serve vital life support functions for patient 110 and it may be configured outside of the MR suite.

If the elements of accessory equipment 201 are to be used during MR scanning it is desirable to make each element of the assembly MR compatible. Two issues with respect to MR compatibility should be considered: A) Ferromagnetic attraction of the element to the magnet, and B) RF interference during MR imaging. While Ferromagnetic attraction can be prevented by maintaining a minimum distance between the magnet and the accessory equipment, RF interference from accessory equipment can degrade MR image quality from anywhere within the MR screen room. The embodiments according to the current disclosure address both issues by providing a location within the screen room that is known to be safe for ferromagnetic equipment, and by preventing (or substantially reducing) interference by RF emissions from the equipment with MR scanning.

In light of the medical importance of accessory assembly 201 to patient 110, it may be desirable to minimize the potential for medical errors that might occur if the accessory assembly needs to be reconfigured for the MR scanning environment (e.g. by switching to an MR-compatible infusion pump). The embodiments according to the current disclosure allow for conventional accessory equipment assemblies 201 (or components thereof) that may not be fully MR compatible to be used safely within the boundaries of the MR screen room.

FIG. 2 also shows the Faraday cage assembly 200 including a Faraday cage 202, which may be comprised of an enclosed cabinet constructed with one or more non-ferromagnetic conducting materials such as copper, aluminum or brass. For purposes of the current disclosure, the "Faraday cage" is an enclosure formed by conducting material or by a mesh of such material (it should be understood that other materials may be utilized in the formation of the Faraday cage as known by those familiar with the state of the art). The conducting material of Faraday cage assembly 200 may be deployed on all surfaces of the Faraday cage 202 in a fashion well-known to those familiar with the state of the art. An additional element of the exemplary Faraday cage 202 is a door 208 and corresponding door-opening 209 and a door frame 207 that allows items such as accessory equipment assembly 201 to be placed inside. Like the walls of the Faraday cage 202, door 208 may be constructed with non-ferromagnetic conducting materials and may have a window 216, which is constructed with conductive glass and/or a conductive mesh screen. Door 208 may incorporate conductive contact fingers 210 to ensure electrical conductivity between the cage and the door frame 207 when the door is closed. Alternatively, door 208 may incorporate an RF gasket to ensure electrical connectivity with the door frame 207. If desired, the contact fingers or an RF gasket can be incorporated into the door frame 207 instead of the door. Door 208 may also include a latch 214 to secure the door when it is closed. It will be appreciated that the Faraday cage 202 may include alternate door components, such as sliding doors and completely removable doors.

The current exemplary Faraday cage assembly 200 includes at least one access slot 212 which provides a means for hoses, wires and similar items ("lines") to exit the cage. In the present embodiment shown in FIG. 2, this slot 212 is placed in the door 208 of the Faraday cage 202 and allows one or more hoses 226 to exit the cage when the door is closed (see FIG. 4, for example). The slot 212 is open on the side of the door 208 and extends inward therefrom (the slot extends inward from the side, top or bottom of the door). In an alternate embodiment, the slot can be provided in the door frame 207 of the Faraday cage 202—again, the slot will be open on an inner side of the door frame 207 and extend outward (into the door frame) therefrom. In yet another embodiment, two such slots can be provided, one in the door 208 and a corresponding slot in the door frame 207 aligned with the door slot. Access slot has the advantage of allowing the door to be closed without detaching the hose because the slot is open to the side, top or bottom of the door or frame. It is also within the scope of the disclosure to provide a notch, groove or other aperture on any side edge or corner of the door, and/or any inner side edge or corner of the door frame (all of which will be referred to herein as a "slot" for brevity). It is recognized that a completely bounded hole in the door or cage wall would provide the same electrical functionality, but require that the hose be detached from the accessory equipment. Consequently, such a completely bounded hole may desirable in some embodiments and undesirable in others. In yet another embodiment the slot can be dispensed with entirely if the conductive contact fingers 210 or RF gasket are soft enough (i.e., compressible) to allow the door 208 to close onto the hoses 226 and other lines extending through the door 208 without impeding the function of the hoses attached to the accessory equipment assembly 201. In such an embodiment the contact fingers 210 or RF gasket will deform over the hoses 26 and/or other lines when the door is being closed allowing the door 208 to close over the hoses 26 and/or other lines.

Faraday cage assembly 200 may have several optional features that ease the use of the system. These include casters 204 that may permit the assembly to be easily moved around the magnet screen room, and a ramp 206 that may permit accessory equipment assembly 201 to be easily moved into the Faraday cage 202. In one embodiment of the present disclosure one or more cage securing points 218 are attached to the Faraday cage 202 to permit the cage to be secured to the wall of the MR system's screen room to prevent the cage from rolling too close to the MRI magnet assembly 102. In alternate embodiments of the current disclosure, casters 204 are not used and the Faraday cage 202 may be permanently fixed in the screen room.

Faraday cage assembly 200 has additional optional features that may prove useful. In one embodiment a power supply 230 may be incorporated into the Faraday cage assembly 200. This power supply may be fully contained within the Faraday cage 202 and provide a battery to power equipment inside the cage, or it can incorporate RF filters that prevent RF interference from exiting the cage via an external power supply cord 232. In this externally-powered configuration, power supply 230 acts as an electrical penetration into the cage. The use of filters in Faraday cage penetration is well known to those skilled in the state of the art. If desired additional filters for communication cables and the like can be incorporated.

Figure 3:
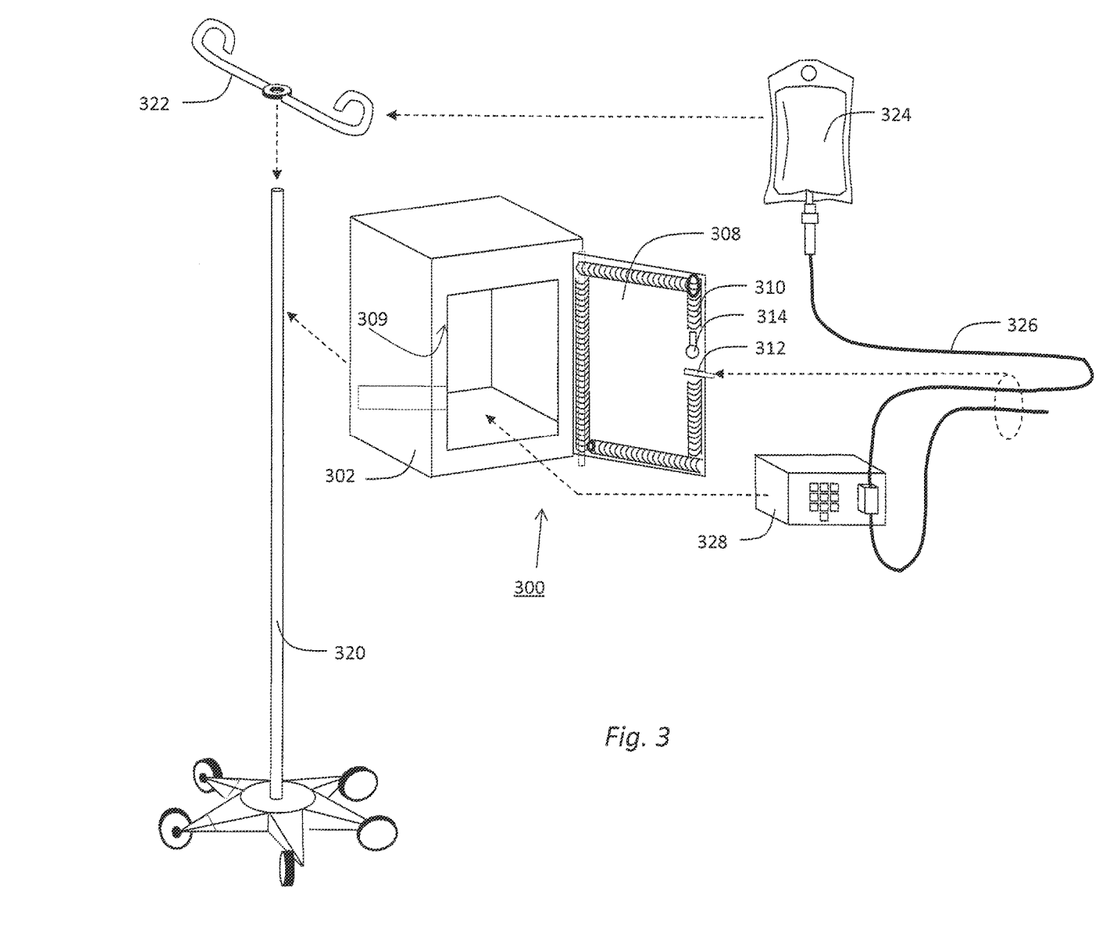
FIG. 3 shows an exemplary portable Faraday cage system suitable for incorporation with an alternate embodiment of the present disclosure.

FIG. 3 shows an alternate embodiment of the Faraday cage assembly 300. In this embodiment, a smaller Faraday cage 302 may be mounted on an IV pole 320. The selected accessory equipment, which for the purposes of this illustration is a free-standing infusion pump 328, is placed inside of the smaller Faraday cage 302. The Faraday cage 302 includes a door 308 and a door opening 309. With the door 308 closed, RF emissions from the free-standing infusion pump 328 may be contained within the Faraday cage and may not significantly interfere with MR image acquisition. The door 308 may include conductive fingers 310, a latch 314, and a slot 312 as described above with respect to the embodiment of FIG. 2. As shown in the embodiment of FIG. 3, an IV bag 324 may be hung on hanger 322 of IV pole 320 on which the Faraday cage 302 is mounted, seated or hung. The infusion pump 328 may be housed within the Faraday cage 302, while portions of IV lines 326 connected between the IV bag 324 and the infusion pump 328 and connected between the infusion pump 328 and the patient (not shown) extend through the slot 312 when the door 308 is closed. Additional options and configurations as discussed herein with respect to the Faraday cage assembly 200 of FIG. 2 may also apply to the embodiment of the Faraday cage assembly 300 of FIG. 3.

Figure 4:
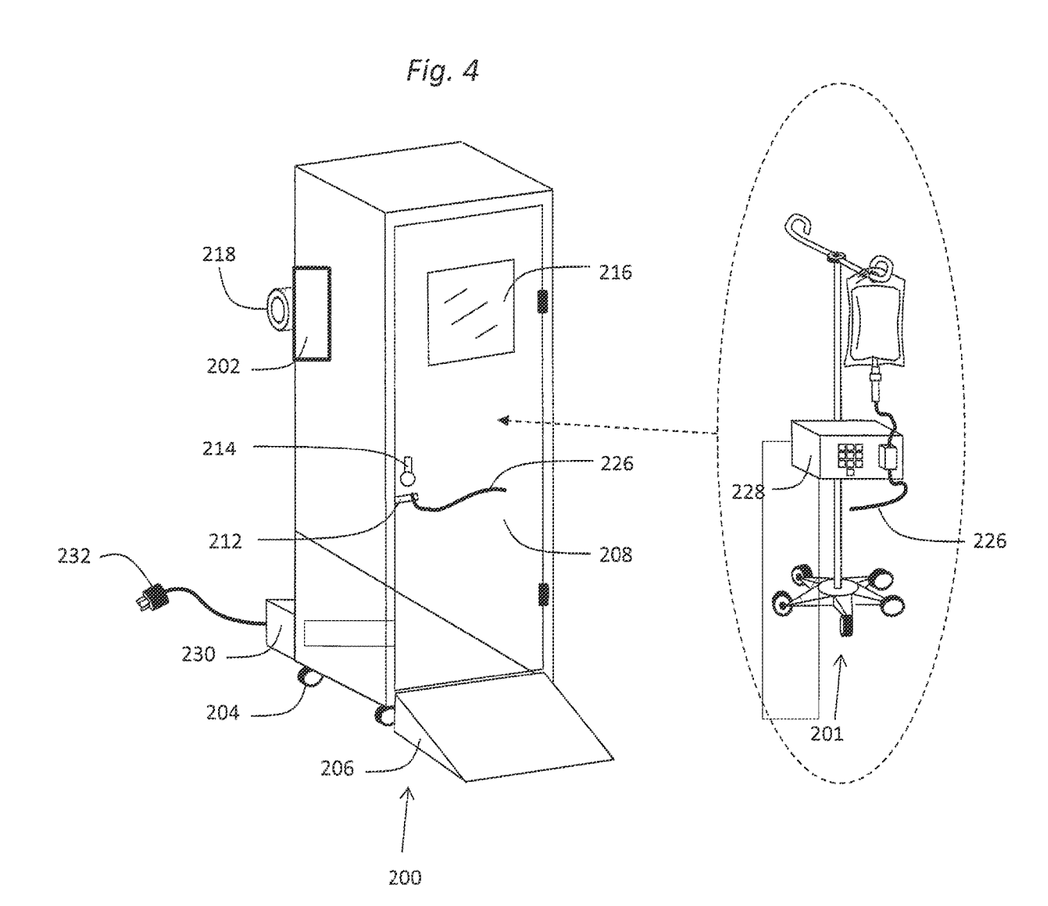
FIG. 4 shows an exemplary portable Faraday cage assembly suitable for incorporation with an embodiment of the present disclosure in which accessory equipment is enclosed.

FIG. 4 shows the Faraday cage assembly 200 of FIG. 2 with its door closed. Inside of the Faraday cage 202 is the selected accessory equipment assembly 201 which, for the purposes of this illustration, includes a single IV hose 226 which is made to exit access slot 212. With the door closed, any RF emissions from infusion pump 228 may be contained within the Faraday cage and may not significantly interfere with MR image acquisition.

Figure 5:
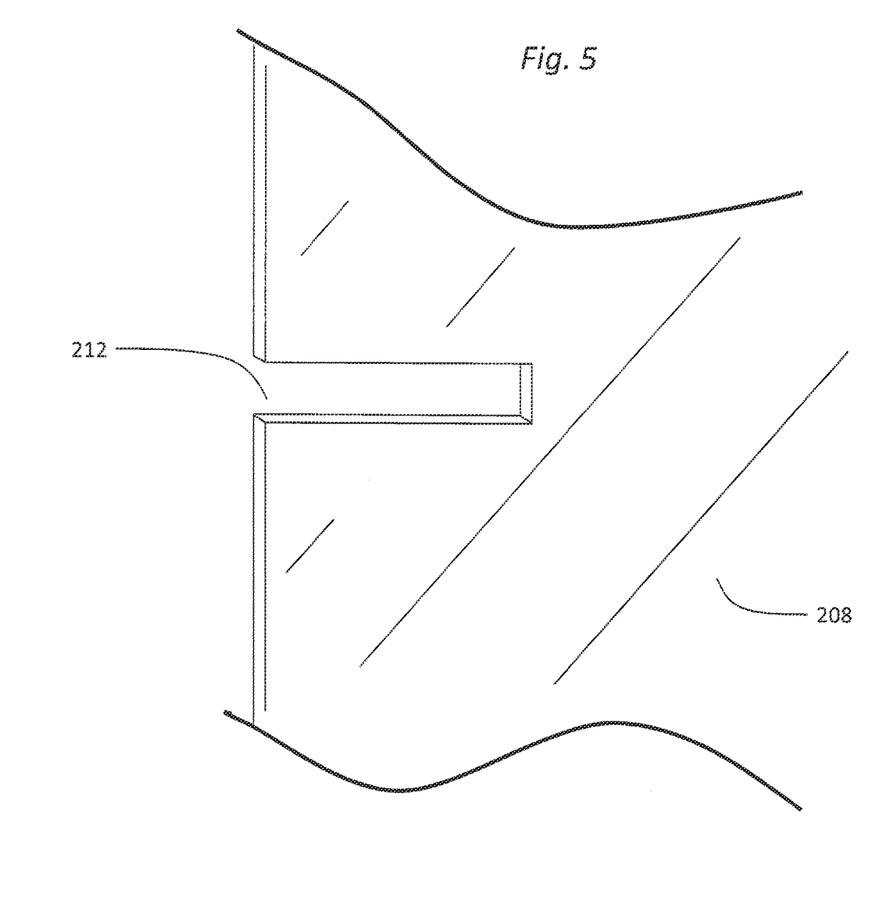
FIG. 5 shows an exemplary construction for a simple access slot in the door of the Faraday cage assembly in accordance with an embodiment of the present disclosure.

FIG. 5 shows a detail of the access slot 212 extending into the edge of the door 208. In this illustration, the point of view is consistent with FIG. 4 and shows the outside of the door. The access slot 212 can be small and should provide adequate RF shielding, for example, if the gap has dimensions (e.g., maximum width) less than approximately $1/4^{th}$ the wavelength of radiofrequency waves at the Larmor frequency of the MR scanner. For example, and without limitation, it has been found that a slot 212 measuring 2 mm×2 mm is adequate for certain MR applications.

Figure 6:
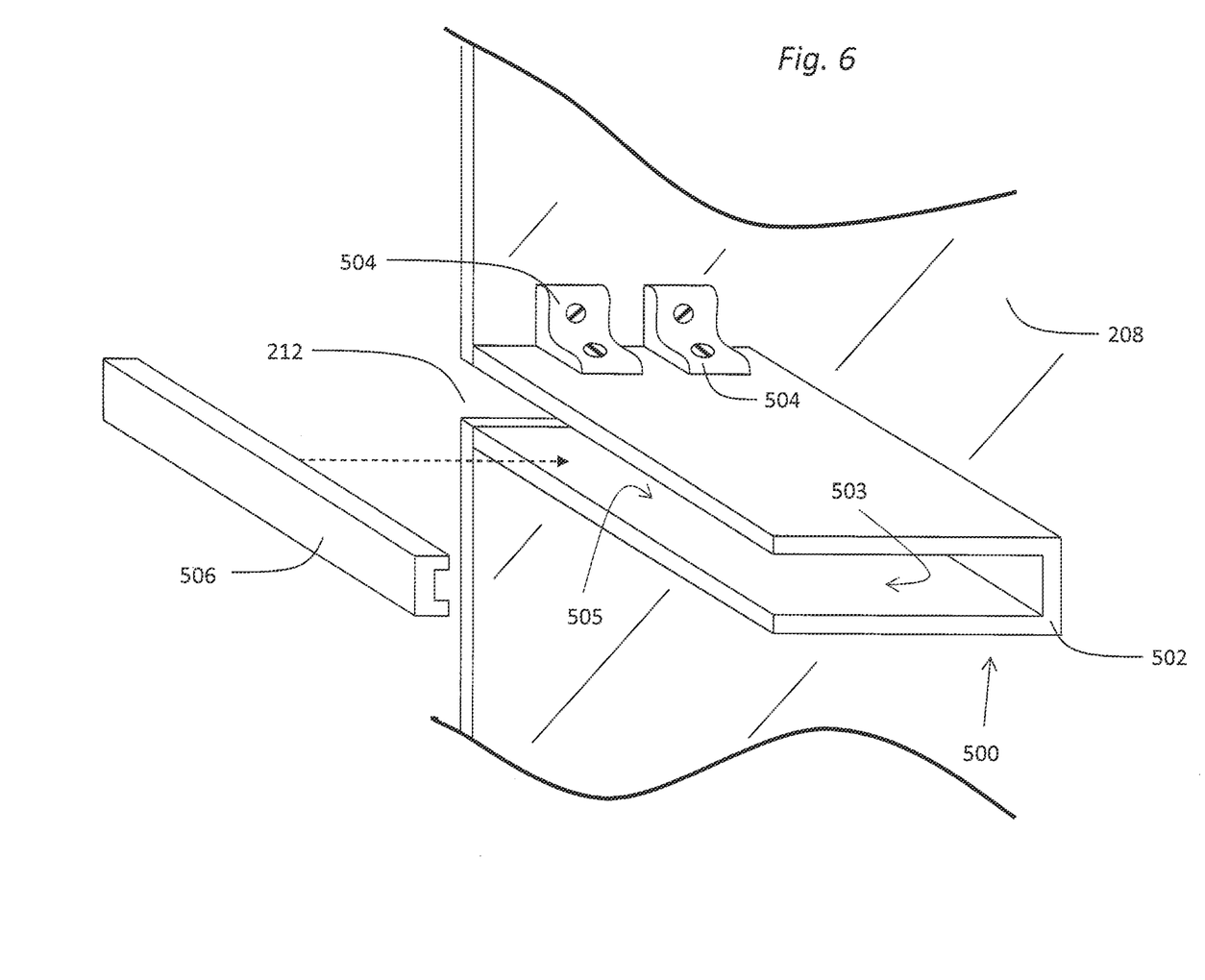
FIG. 6 shows an exemplary construction for an external waveguide mounted to an access slot in the door of the Faraday cage assembly in accordance with an embodiment of the present disclosure.

FIG. 6 shows an alternate embodiment of the current disclosure in which an external waveguide assembly 500 is attached to access slot 212. In this embodiment the waveguide is comprised of an external elongated waveguide body 502 which is attached to the door 208 with external waveguide mounting hardware 504 shown here as a pair of angle brackets. The elongated waveguide body 502 is generally c-shaped in cross-section and provides an elongated waveguide channel 503 extending therethrough and a longitudinal side opening 505. An external waveguide cap 506 can be placed into the side opening 505 once the hose or tube is placed in the waveguide channel 503 to provide a conducting surface around the entire hose. The cross-sectional maximum width of the waveguide channel 503 (when the cap 506 is placed over it) is desirably less than approximately $1/4^{th}$ the wavelength of radiofrequency waves at the Larmor frequency of the MR scanner. The length of the waveguide body 502 and cap 506 is desirably longer than approximately $1/4^{th}$ the wavelength of radiofrequency waves at the Larmor frequency of the MR scanner.

Figure 7:
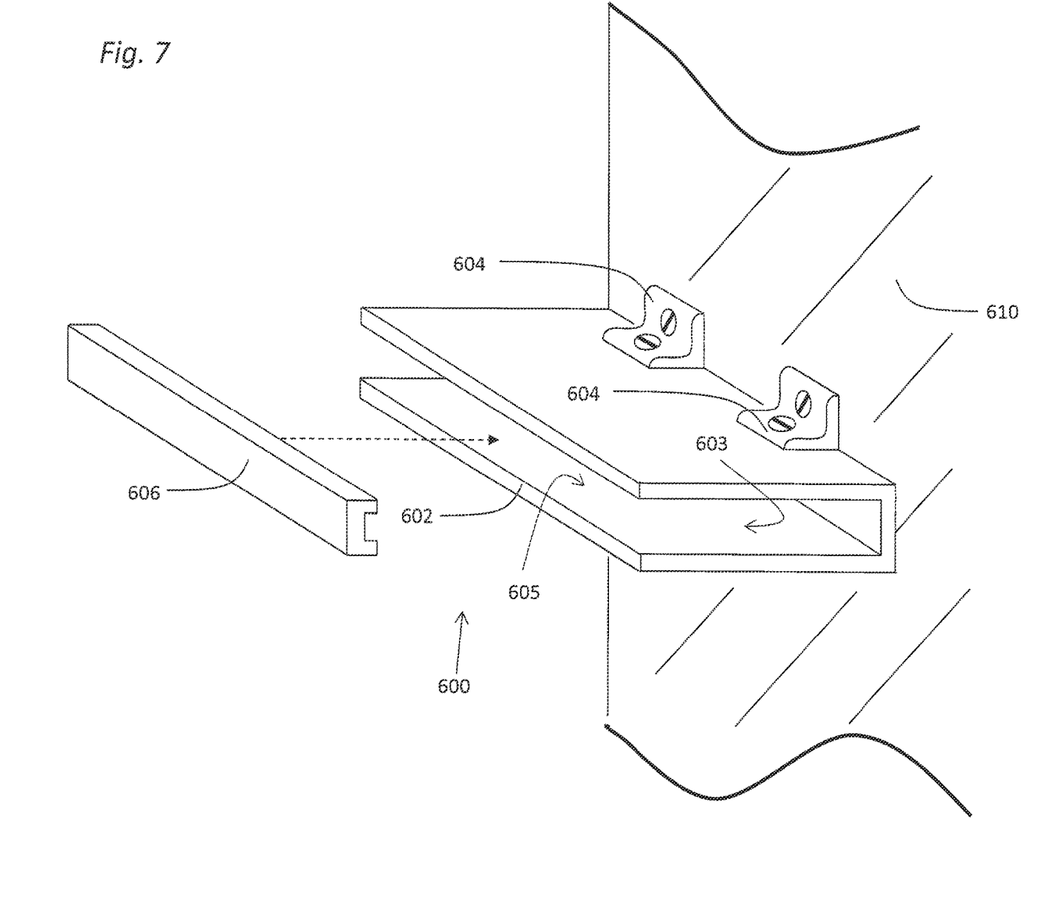
FIG. 7 shows an exemplary construction for an internal waveguide mounted to the wall of the Faraday cage assembly in accordance with an embodiment of the present disclosure.

FIG. 7 shows an alternate embodiment of the current disclosure in which an internal waveguide assembly 600 is attached to an interior wall of Faraday cage assembly 200. In this illustration, the point of view is from the inside of the cage looking out through the door frame. In this embodiment, the waveguide is comprised of an internal waveguide body 602 which is attached to an internal wall 610 of the Faraday cage with internal waveguide mounting hardware 604 shown here as a pair of angle brackets. The elongated waveguide body 602 is generally c-shaped in cross-section and provides an elongated waveguide channel 603 extending therethrough and a longitudinal side opening 605. An internal waveguide cap 606 can be placed into the side opening 605 once the hose or tube is placed in the waveguide channel to provide a conducting surface around the entire hose. The cross-sectional maximum width of the waveguide channel 603 (when the cap 606 is placed over it) is desirably less than approximately $1/4^{th}$ the wavelength of radiofrequency waves at the Larmor frequency of the MR scanner. The length of the waveguide body 602 and cap 606 is desirably longer than approximately ¼th the wavelength of radiofrequency waves at the Larmor frequency of the MR scanner.

Figure 8:
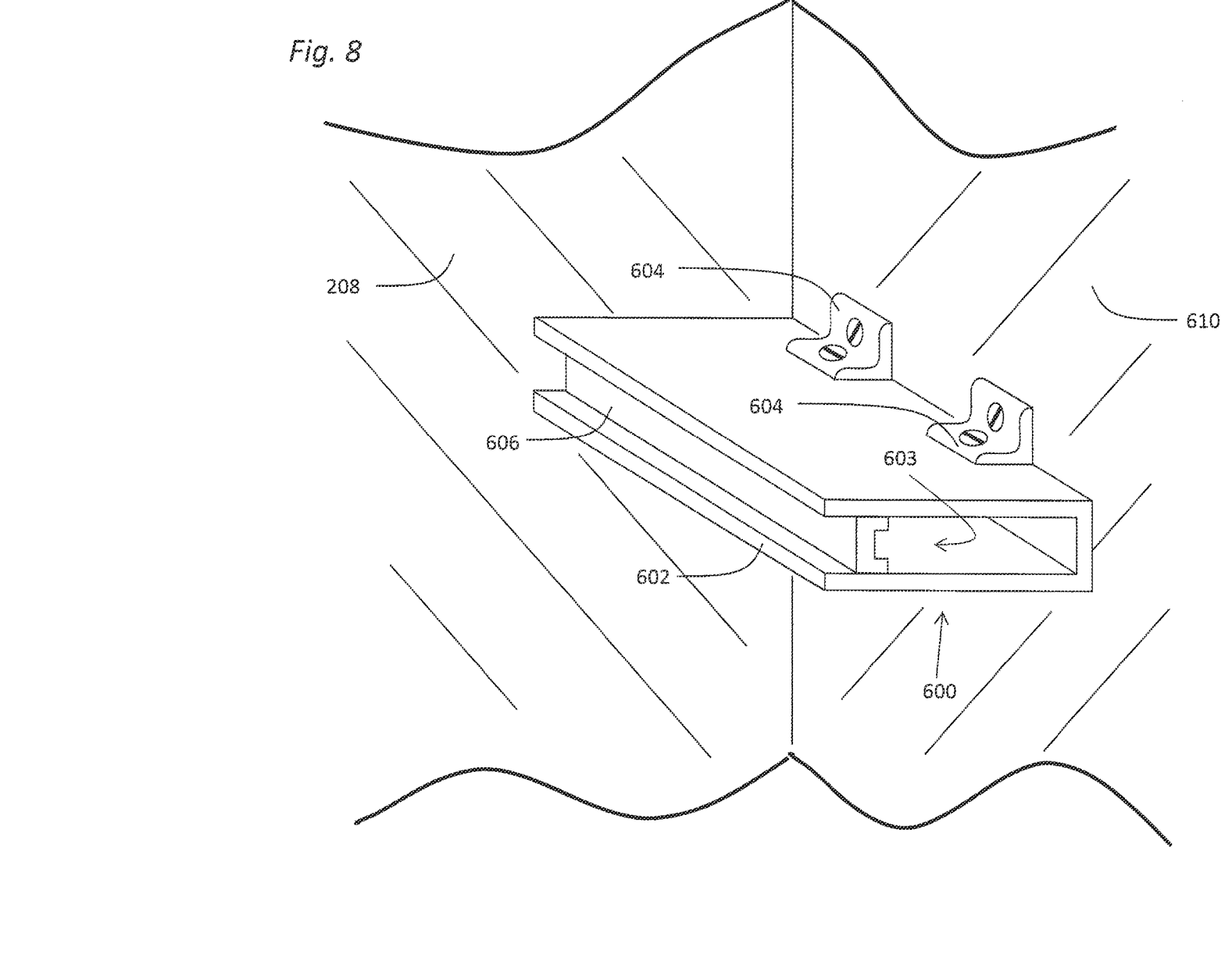
FIG. 8 shows the exemplary construction for an internal waveguide described in FIG. 7 with the door to the Faraday cage closed in accordance with an embodiment of the present disclosure.

FIG. 8 shows the embodiment of the current disclosure illustrated in FIG. 7 with the added element of a closed door. In this embodiment, the internal waveguide assembly 600 abuts the closed door and the slot in the waveguide aligns with access slot 212. Note that internal waveguide cap 606 can be manually placed into the gap before the door is closed, or it can be made to be an integral part of the door so that it automatically aligns with the internal waveguide body 602 when the door is closed.

Figure 9:
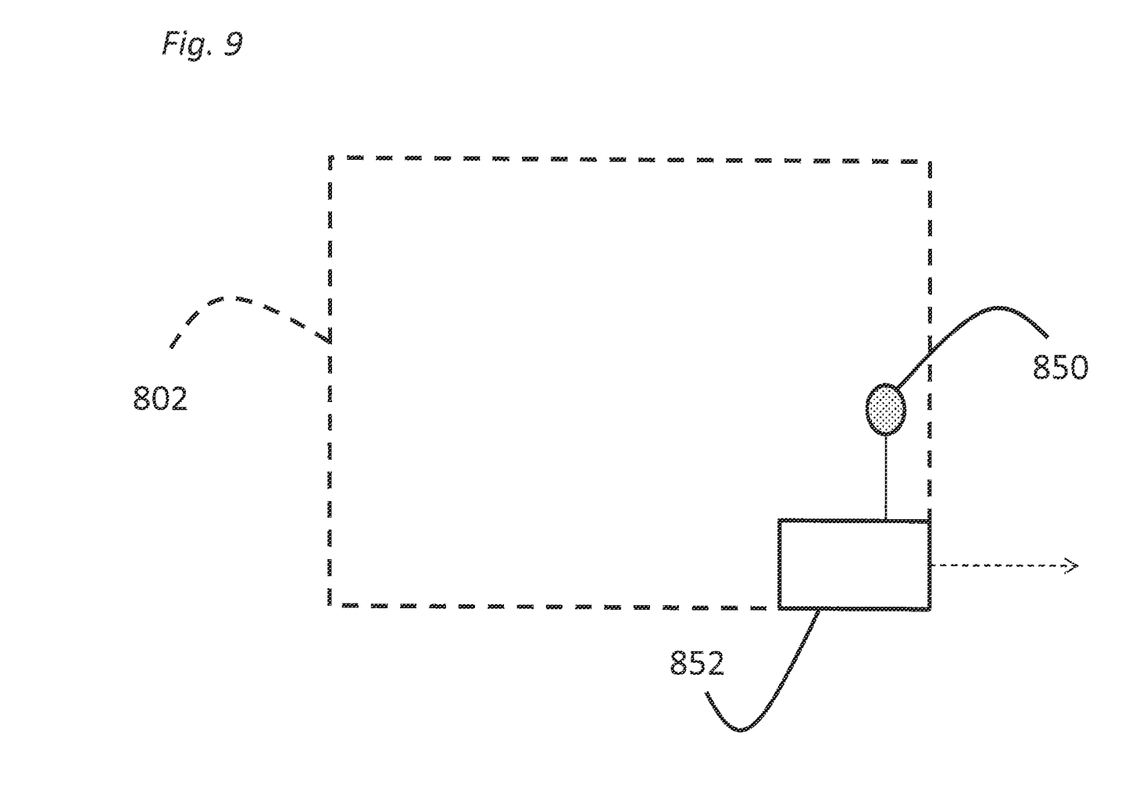
FIG. 9 shows a block diagram representation of an exemplary Faraday box including a microphone and transmitter device.

FIG. 9 shows an embodiment of the current disclosure in which a Faraday cage 802 is equipped with an internal microphone 850, which is in turn electrically connected to a transmitter component 852. The microphone 850 and transmitter 852 assembly may be used, for example, to receive audible indicators and alarms from equipment operating in the Faraday cage 802 and transmit (wirelessly for example) the audible indicator/alarm to a receiver external to the Faraday cage. In such a configuration, alarms emitted by an IV pump, for example, may be transmitted to a speaker system, for example, of the MR suite so that practitioners will be able to hear the alarm. Alternatively, the transmitter 852 may transmit information indicative of a received alarm to an external computer or control system, which may process the information so that the practitioners, nurses, assistants and the like are appropriately notified. In an exemplary embodiment, the transmitter 852 may be a Bluetooth repeater, which transmits using frequencies much higher than the Larmor frequencies of the MR scanner, and which are not effectively blocked by the Faraday cage 802. In an alternate embodiment, the transmitter 852 may include an electronic intercom.

Figure 10:
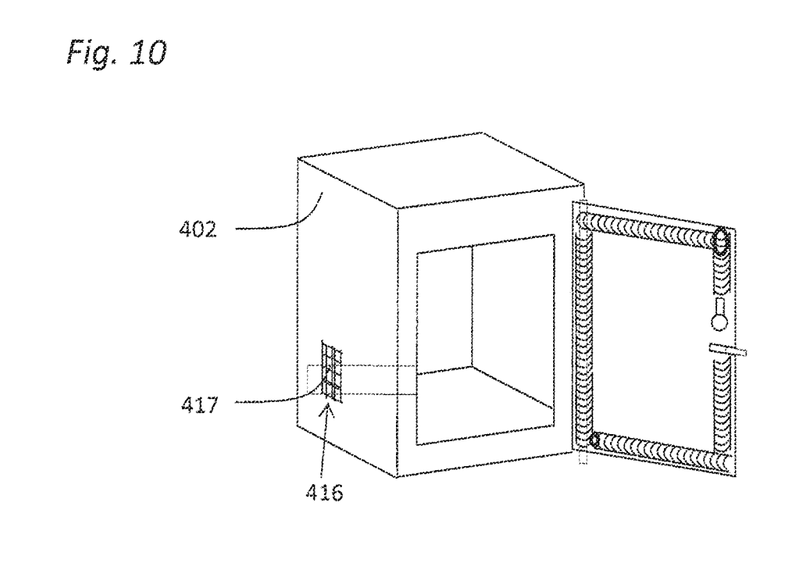
FIG. 10 shows an exemplary Faraday cage incorporating a mesh screened window.

FIG. 10 shows an embodiment of the current disclosure in which a Faraday cage 402 includes a window 416 covered by a mesh screen 417 to allow sounds emitted within the Faraday cage 402 to be heard outside of the Faraday cage 402. In such an embodiment the screen 417 is conductive and electrically connected to the walls of the Faraday cage. The size of the holes in the screen determine the upper bound of frequencies that are contained in the device (smaller holes will make the Faraday cage 402 block higher frequencies). With MR, the band of frequencies desired to block is narrow and is set by the Larmor frequency of the scanner.

While the foregoing disclosure includes many details and specificities, it is to be understood that these have been included for purposes of explanation and example only, and are not to be interpreted as limitations of the inventions described herein. It will be apparent to those skilled in the art that other modifications to the embodiments described above can be made without departing from the spirit and scope of the inventions as claimed. Accordingly, such modifications are to be considered within the scope of such inventions. Likewise, it is to be understood that it is not necessary to meet any or all of the identified advantages or objects of any of the inventions described herein in order to fall within the scope of the claims, since inherent and/or unforeseen advantages of such inventions may exist even though they may not have been explicitly discussed herein.

All publications, articles, patents and patent applications cited herein are incorporated into the present disclosure by reference to the same extent as if each individual publication, article, patent application, or patent was specifically and individually indicated to be incorporated by reference.

What is claimed is:

1. An assembly for housing a patient's treatment or monitoring equipment during a patient's Magnetic Resonance (MR) exam, comprising:
a Faraday cage having an interior sized for receiving a patient's treatment or monitoring equipment, the Faraday cage having a door-opening into the interior and a door adapted to cover the door-opening.

2. The assembly of claim 1, further comprising:
a slot opening and extending into at least one of (a) an outer side edge of the door and (b) an inner side edge of the door-opening, the slot providing an opening into the Faraday cage interior when the door is closed that is sized to receive lines extending between the patient and patient's treatment or monitoring equipment.

3. The assembly of claim 2, wherein the slot is dimensioned to block RF signals below a predetermined frequency.

4. The assembly of claim 3, wherein the predetermined frequency is higher than the Larmor frequency of an MR scanner used for the patient's MR exam.

5. The assembly of claim 3, wherein the opening provided by the slot has a maximum opening width dimension of less than ¼th the wavelength of radio frequency waves at the Larmor frequency of an MR scanner used for the patient's MR exam.

6. The assembly of claim 2, further comprising a waveguide assembly mounted thereto and having a waveguide channel extending therethrough and sized to receive lines extending between the patient and patient's treatment or monitoring equipment, the waveguide channel communicating with the slot opening into the Faraday cage.

7. The assembly of claim 6, wherein the waveguide assembly includes:
an elongated waveguide body having a longitudinal side opening into the waveguide channel for receiving the lines extending between the patient and patient's treatment or monitoring equipment therein; and
an elongated cap adapted to mount over the longitudinal side opening of the waveguide body.

8. The assembly of claim 6, wherein the waveguide assembly is mounted within the Faraday cage.

9. The assembly of claim 6, wherein the waveguide assembly is mounted to one of an inner surface and outer surface of the door.

10. The assembly of claim 6, wherein the length of the waveguide body is longer than approximately ¼th the wavelength of radio frequency waves at the Larmor frequency of an MR scanner used for the patient's MR exam.

11. The assembly of claim 6, wherein the waveguide channel has a maximum cross-sectional width dimension of less than ¼th the wavelength of radio frequency waves at the Larmor frequency of an MR scanner used for the patient's MR exam.

12. The assembly of claim 1, wherein the Faraday cage interior is sized to receive an accessory equipment assembly including an IV pole, an IV bag holder, an IV bag, and an infusion pump.

13. The assembly of claim 12, further comprising a ramp providing a slanted surface from a floor surface on which the assembly is situated to a bottom surface of the Faraday cage interior.

14. The assembly of claim 12, further comprising rollers mounted on an underside surface of the Faraday cage.

15. The assembly of claim 1, wherein the Faraday cage is adapted to be mounted to, seated on, or hung from an IV pole.

16. The assembly of claim 1, further comprising a power supply, the power supply providing electrical outlets to the Faraday cage interior.

17. The assembly of claim 16, wherein the power supply is contained within the Faraday cage interior.

18. The assembly of claim 16, wherein the power supply includes and external power supply cord and RF filters that substantially limit RF interference from exiting the Faraday cage via the external power supply cord.

19. The assembly of claim 16, wherein the power supply includes an internal battery providing power to the electrical outlets.

20. The assembly of claim 1, wherein the door-opening comprises a door frame and the assembly further comprises a conductor mounted to one or more of the door and the door frame, providing electrical contact between the door and the door frame when the door is closed onto the door frame.

21. The assembly of claim 20, wherein the conductor comprises a plurality of conducting fingers affixed to one or more of the inside surface of the door and the outer surface of the door frame.

22. The assembly of claim 20, wherein the conductor comprises a conductive gasket affixed to one or more of the inside surface of the door and the outer surface of the door frame.

23. The assembly of claim 20, wherein the conductor is sufficiently compressible to deform over lines connected between the patient's treatment or monitoring equipment received within the Faraday cage interior and the patient and extending through the door-opening when the door is closed.

24. The assembly of claim 1, further comprising a window enclosing a window pane providing visual access to the Faraday cage interior, the window pane being formed from a conductive material.

25. The assembly of claim 24, wherein the window is provided on the door.

26. The assembly of claim 1, further comprising a screened window providing audible access to the Faraday cage interior, the screen being comprised of a conductive mesh electrically coupled to at least one of a Faraday cage wall and a Faraday cage door.

27. The assembly of claim 1, further comprising an audio transmission system for transmitting audio sounds emanating from the Faraday cage interior to a point outside of the Faraday cage.

28. The assembly of claim 27, wherein the audio transmission system includes a microphone positioned within the Faraday cage interior.

29. The assembly of claim 28, wherein the audio transmission system includes a Bluetooth repeater in electrical communication with the microphone.

30. The assembly of claim 28, wherein the audio transmission system includes an electronic intercom.

31. The assembly of claim 1, further comprising:
a 2 mm×2 mm slot opening and extending into at least one of (a) an outer side edge of the door and (b) an inner side edge of the door-opening, the slot providing an opening into the Faraday cage interior when the door is closed that is sized to receive lines extending between the patient and patient's treatment or monitoring equipment.

32. The assembly of claim 1, wherein the Faraday cage is constructed primarily from non-ferromagnetic materials.

33. The assembly of claim 32, wherein the non-ferromagnetic material include copper.

34. The assembly of claim 32, wherein the non-ferromagnetic material include aluminum.

35. The assembly of claim 32, wherein the non-ferromagnetic material include brass.

36. A method for performing a Magnetic Resonance exam on a patient connected by a line to a piece of medical equipment, comprising the steps of:
providing a Faraday cage assembly including:
a Faraday cage having an interior sized for receiving the piece of medical equipment, the Faraday cage having a door-opening into the interior and a door adapted to cover the door-opening; and
a slot opening and extending into at least one of (a) an outer side edge of the door and (b) an inner side edge of the door-opening, the slot providing an opening into the Faraday cage interior when the door is closed that is sized to receive the lines extending between the patient and patient's piece of medical equipment;
placing the piece of medical equipment into the Faraday cage interior,
inserting the lines extending between the patient and the piece of medical equipment into the slot;
closing the door; and
performing the MR exam on the patient while the piece of medical equipment is in the Faraday cage interior with the door closed;
wherein the above steps occur without disconnecting the lines from the piece of medical equipment or from the patient.

37. A Faraday cage system for use with a Magnetic Resonance (MR) scanner comprising:
a Faraday cage assembly deployed within the screen room of said MR scanner wherein said cage assembly is capable of housing accessory medical equipment;
a door attached to the Faraday cage assembly for installing, accessing and removing said accessory medical equipment.

38. The Faraday cage assembly of claim 37, wherein casters are affixed to the assembly to facilitate movement of the cage.

39. The Faraday cage assembly of claim 37, wherein a ramp is provided to ease the movement of the accessory medical equipment into and out of the cage.

40. The Faraday cage assembly of claim 37, wherein conducting fingers are affixed to at least one the door and a door-frame of the Faraday cage to provide electrical contact between the door and the body of the cage.

41. The Faraday cage assembly of claim 37, wherein a conducting gasket is affixed to at least one of the door and a door-frame of the Faraday cage to provide electrical contact between the door and the body of the cage.

42. The Faraday cage assembly of claim 37, wherein at least one of a conducting gasket and conducting fingers are affixed to at least one the door and a door-frame of the Faraday cage to provide electrical contact between the door and the body of the cage, and the at least one of the conducting gasket and conducting fingers are sufficiently compressible to deform over accessory medical equipment lines extending through the door-frame when the door is closed.

43. The Faraday cage assembly of claim 37, wherein a conducting window is incorporated into the door to provide visual access to the accessory medical equipment when the door is closed.

44. The Faraday cage assembly of claim 37, wherein an attachment point is affixed to the body of the cage to provide a means to restrict motion of the cage within the MR scanner's screen room.

45. The Faraday cage assembly of claim 37, wherein a power supply is affixed to the body of the cage to provide power to the accessory medical equipment when the door is closed.

46. The Faraday cage assembly of claim 45, wherein the power supply is incorporates a battery.

47. The Faraday cage assembly of claim 45, wherein the power supply incorporates a power supply cord suitable for attachment to an external power source.

48. The Faraday cage assembly of claim 45, wherein the power supply incorporates a filter to prevent radiofrequency interference generated by the accessory medical equipment inside the cage from exiting the cage.

49. The Faraday cage assembly of claim 37, wherein the door has a latch to secure the door in the closed position.

50. The Faraday cage assembly of claim 37, wherein an access slot in at least one of the door and a door-frame to the Faraday cage permits an accessory medical equipment line to exit the Faraday cage assembly when the door is closed.

51. The Faraday cage assembly of claim 50, wherein a waveguide is affixed to the access slot.

52. The Faraday cage assembly of claim 50, wherein a waveguide is affixed to the interior of the cage, said waveguide being aligned with the access slot to permit the accessory medical equipment line to exit the Faraday cage assembly when the door is closed.

53. The Faraday cage assembly of claim 52, wherein a waveguide cap is provided to completely surround the accessory medical equipment line with electrically conducting material.

54. The Faraday cage assembly of claim 53, wherein the waveguide cap attached to the door.

55. The Faraday cage assembly of claim 37, wherein the accessory medical equipment includes at least one of an infusion pump, a patient monitor, a power injector, a respirator and an anesthesia delivery system.

56. The Faraday cage assembly of claim 37, wherein the body of the Faraday cage is primarily constructed from non-ferromagnetic material.

57. The Faraday cage assembly of claim 56, wherein the non-ferromagnetic material is at least one of copper, aluminum and brass.

58. The Faraday cage assembly of claim 37, further comprising a screened window providing audible access to an interior of the Faraday cage, the screen being comprised of a conductive mesh electrically coupled to at least one of a Faraday cage wall and the door.

* * * * *